United States Patent [19]

Hyon et al.

[11] Patent Number: 5,100,669
[45] Date of Patent: Mar. 31, 1992

[54] POLYLACTIC ACID TYPE MICROSPHERES CONTAINING PHYSIOLOGICALLY ACTIVE SUBSTANCE AND PROCESS FOR PREPARING THE SAME

[75] Inventors: Suong-Hyu Hyon; Yoshita Ikada, both of Uji, Japan

[73] Assignee: Biomaterials Universe, Inc., Kyoto, Japan

[21] Appl. No.: 315,167

[22] Filed: Feb. 24, 1989

[30] Foreign Application Priority Data

Feb. 24, 1988 [JP] Japan .................. 63-42459

[51] Int. Cl.$^5$ .................. A61K 9/50; B01J 13/12
[52] U.S. Cl. .................. 424/426; 427/213.36; 424/489; 424/497; 428/402.24; 514/963
[58] Field of Search .................. 264/4.1, 4.6; 427/213.36; 424/489, 490, 497, 501, 499, 426

[56] References Cited

U.S. PATENT DOCUMENTS

| | | | |
|---|---|---|---|
| 4,389,330 | 6/1983 | Tice et al. | 427/213.36 |
| 4,479,911 | 10/1984 | Fong | 264/4.6 |
| 4,492,720 | 1/1985 | Mosier | 427/213.3 |
| 4,542,025 | 9/1985 | Tice et al. | |
| 4,622,244 | 11/1986 | Lapka et al. | 427/213.32 |
| 4,637,905 | 1/1987 | Gardner | 264/4.1 |
| 4,675,189 | 6/1987 | Kent et al. | 424/490 |
| 4,832,686 | 5/1989 | Anderson | 264/4.6 X |
| 4,835,139 | 5/1989 | Tice et al. | 514/800 X |
| 4,849,228 | 7/1989 | Yamamoto et al. | 264/4.6 X |
| 4,853,226 | 8/1989 | Machida et al. | 424/499 X |

FOREIGN PATENT DOCUMENTS

| | | |
|---|---|---|
| 0058481 | 8/1982 | European Pat. Off. . |
| 0134318 | 3/1985 | European Pat. Off. . |
| 0145240 | 6/1985 | European Pat. Off. . |
| 0274961 | 7/1988 | France . |

*Primary Examiner*—Richard D. Lovering
*Assistant Examiner*—John M. Covert
*Attorney, Agent, or Firm*—Birch, Stewart, Kolasch & Birch

[57] ABSTRACT

Microspheres comprising polylactic acid and a water soluble physiologically active substance and having a mean particle size of from about 0.01 μm to 300 μm, which show not more than 30% of an eluted amount of said physiologically active substance based on the content of said physiologically active substance in the polylactic acid type microspheres after 24 hours in in vitro elution test in phosphate buffer of pH 7.4 at 37° C., and a process for preparing the same. The polylactic acid type microspheres of this invention is advantageous in that the active substance can be uniformly incorporated into the microspheres without loss of the activity, can gradually release the active substance for a long time of period of more than one week.

6 Claims, No Drawings

POLYLACTIC ACID TYPE MICROSPHERES CONTAINING PHYSIOLOGICALLY ACTIVE SUBSTANCE AND PROCESS FOR PREPARING THE SAME

The present invention relates to release-controlled polylactic acid type microspheres containing a water soluble physiologically active substance and a process for preparing the same.

TECHNICAL BACKGROUND AND PRIOR ART

There is an increasing interest in developing a new drug delivery system (DDS) in recent years. This is due to a social requirement for attaining both safety and high biological availability of drug, i.e. to maximize pharmaceutical activity of known drugs as well as to minimize side effects thereof. In the DDS study, a commonly employed pharmaceutical carrier is a nondegradable high molecular weight compound such as silicone rubber, polyethylene or ethylene-vinyl acetate copolymer. These carriers have given a good result in a percutaneous preparation which is administered through the skin or mucosa. However, when these high molecular weight compounds are implanted or injected into the human body, these carriers remain in the body as a foreign material after release of the drug, which causes a certain amount of trouble for the body. On the contrary, if a high molecular weight compound degradable and absorbable in vivo is employed as the carrier, the carrier is gradually hydrolyzed in the living tissue and simultaneously the drug contained therein is gradually released, and hence, surgical treatment is not required to take out the carrier after the treatment.

The high molecular weight compound degradable and absorbable in vivo includes a natural high molecular weight compound, a typical example of which is collagen, and a synthetic high molecular weight compound, a typical example of which is polylactic acid. The polylactic acid is synthesized from lactic acid which is widely distributed in nature. Besides, this polylactic acid is nonenzymatically hydrolized in vivo and finally exhausted as carbon dioxide and water, and hence, it is an interesting high molecular weight compound degradable and adsorbable in vivo. It has been, therefore, studied as a release-controlling carrier for various drugs since the 1970s [Suong-Hyu Hyon, Seiyaku Kojo (Pharmaceutical Factory), Vol. 13, No. 10, p552, 1983].

Among the known studies, a representative one is a process which comprises dissolving a hydrophobic drug such as a hormone drug (e.g. estradiol, and the like) in an organic solvent such as benzene together with the polylactic acid and then removing the solvent by distillation to formulate a film, powder, pellet and the like (Japanese Patent Second Publication No. 17525/1975). There is also known a so-called solvent evaporation drying method which comprises dissolving the polylactic acid and the hydrophobic drug in an organic solvent for dissolving both components, adding a phase-separating agent to the solution to cause emulsification and then removing the solvent by distillation to collect microparticles (Japanese Patent First Publication No. 33414/1980). However, these methods are applicable only to hydrophobic drugs since they employ a hydrophobic organic solvent such as benzene, chloroform, or the like.

On the other hand, for a release-controlled preparation of a water soluble drug by the polylactic acid type high molecular weight compound, the following procedures have been attempted. Japanese Patent First Publication No. 100516/1985 discloses a procedure wherein a three-layer emulsion of W/O/W type is formed and subjected to drying in water to give microcapsules of polylactic acid. However, this procedure has various disadvantages, i.e. a troublesome process for preparation, a requirement of the third component such as gelatin, in addition to the drug and the polylactic acid, difficulty to obtain microspheres in submicron order and a low rate of incorporation of the drug into capsules due to three-layer structure, and occurance of burst induced by damage of the polylactic acid wall of the microsphere due to a thin wall of the microcapsules, which results in an unstable release of the drug.

Japanese Patent First Publication No. 150609/1982 describes in detail a sustained release of a polypeptide stable to an acid wherein hydrophobic polylactic acid and a hydrophilic polypeptide are dissolved in a mixture of dioxane and water. However, since at least one of the polylactic acid and the polypeptide is not completely dissolved in the mixture, the obtained solution is not clear. Further, in order to avoid undesirable ununiformity of the polylactic acid and the polypeptide, a film prepared by a casting method is further subjected to a compression molding with a hot press to formulate into a polypeptide-containing polylactic acid film, sheet, cylinder, or pulverized product thereof. Although glacial acetic acid is employed as a solvent of the polylactic acid, a mixed solution of the polylactic acid and the polypeptide is lyophilized and then subjected to an extrusion molding at a high temperature to formulate in a cylinder shape. Thus, this literature does not teach a formulation of the microsphere having a particle size of from 0.01 $\mu$m to 300 $\mu$m like in the present invention.

As is clear from the above description, these known inventions provide with DDS systems having some effects, but are disadvantageous in that they cannot prepare microspheres wherein the hydrophilic physiologically active substance and hydrophobic polylactic acid are uniformly mingled in a molecular order, or in that they include a troublesome procedure for preparation.

SUMMARY OF THE INVENTION

Under such circumstances, the present inventors have intensively studied to develop an improved process for preparing of a release-controlled polylactic acid type preparation which is simple and can afford a stable release of an active substance, and have found that there can be obtained a microspherical preparation which can attain a sustained release of an active substance for a long period of time with avoiding the undesirable occurrence of bursting. The process is directed to preparing a solution of a water soluble physiologically active substance and polylactic acid uniformly dissolved in a mixed solvent comprising a hydrophilic organic solvent and water or in an organic acid, mixing the solution with a poor solvent which is immiscible with said mixed solvent or organic acid to give an emulsion, and then subjecting the mixture to solvent evaporation drying.

An object of the present invention is to provide polylactic acid type microspheres containing a water soluble physiologically active substance, having a high rate of incorporation of employed active substance into said microspheres, and having a mean particle size of from about 0.01 μm to about, 300 μm, showing, in in vitro elution test in phosphate buffer of pH 7.4 at 37° C., not more than 30% of an eluted amount of said physiologically active substance based on the content of said physiologically active substance in the polylactic acid type microspheres after 24 hours, and thus enabling a stable sustained release of the active substance over a long period of time.

Another object of the present invention is to provide a process for preparing polylactic acid type microspheres containing a water soluble physiologically active substance, which comprises preparing a solution of the water soluble physiologically active substance and the polylactic acid uniformly dissolved in a mixed solvent comprising a hydrophilic organic solvent and water or in an organic acid, mixing the solution with a poor solvent which is immiscible with said mixed solvent or organic acid to give an O/O type or W/O type emulsion, and then subjecting the mixture to the solvent evaporation drying. These and other objects and advantages of the present invention will be apparent to persons skilled in the art from the following description.

DETAILED DESCRIPTION OF THE INVENTION

The "water soluble physiologically active substance" in the present invention is preferably a drug showing a high hydrophilicity and a low partition rate in oil and water, but includes those compatible with both oil and water. Such a drug includes, for example, hydrophilic anticancer drugs, antibiotics, polypeptides having a physiological activity, antipyretics, sedatives, immunoactivators, antiinflammatory agents, antitussives, antiepileptics, antihistaminics, hypotensives, diuretics, antidiabetics, muscle relaxants, antiulcer agents, antidepressants, anti-allergic agents, cardiotonics, antiarrhythmic agents, vasodilating agents, anticoagulating agents, narcotic antagonists, hemostatic agents, antitubercular agents, hormones, and the like.

Preferable examples of the anticancer agents are adriamycin, mitomycin, bleomycin, cisplatin, 5-fluorouracil, methotrexate, actinomycin D, crestin, picibanil, lentinan, and the like. The polypeptides having a physiological activity include, for example, insulin, somatostatin, luteinizing hormone releasing hormone (LHRH) and a derivative of LHRH, prolactin, adrenocorticotropic hormone (ACTH), growth hormone (GH), thyroid-stimulating hormone releasing hormone, melanocyte-stimulating hormone (MSH), luteinizing hormone (LH), palipresin, calcitonin, oxytocin, accessory thyroid hormone, gastrin, tetragastrin hydrochloride, glucagon, pancreozymin, cholecystokinin, angiotensin, human placental lactogen, human chorinic gonadotropin (HCG), enkephalin, endorphin, keutorphin, interferon, interleukin (I, II, III), tumor necrotizing factor (TNF), tuftsin, thymopoietin, thymosin, thymostimulin, thymic humoral factor, blood thymic factor, colony stimulating factor, motiline, deinorphin, bompesin, neurotensin, cerulein, bradykinin, urokinase, asparaginase, kallikrein, substance P, nerve growth factor, blood coagulating factor, lysozyme chloride, polymyxin B, colistin, glamicidin, bacitracin, and the like.

The antibiotics include, for example, tetracyclines (TCs) such as chlortetracycline (CTC), oxytetracycline (OTC), doxycycline (DOXY) and tetracycline (TC); a variety of penicillins (PCs); cephalosporins (CEPs); streptomycin, novabiosin, neomycin, erythromycin, colistin, lincomycin, nalidixic acid, aburamycin, salinomycin, nigericin, kanamycin, kitosamycin, tylosin, furaltadone, vancomycin, thiostrepton, gentamycin, tobramycin, spiramycin, ristocetin, seumycin, erythromycin, 5-O-mycaminoturutyronorid, dibekacin hydrochloride, and the like.

The antipyretic, analgesic, antiinflammatory agents include, for example, sodium salicylate, sulpyrin, diclofenac sodium, indomethacin sodium, sodium flufenamate, pethidine hydrochloride, morphine hydrochloride, oxymorphone, levorphanol tartrate, and the like.

The sedatives include, for example, prochlorperazine, trichlorperazine, chlorpromazine hydrochloride, atropine sulfate, scopolamine methylbromide, and the like.

The antitussive expectorants include, for example, noscapine hydrochloride, codeine phosphate, methylephedrine hydrochloride, ephedrine hydrochloride, alloclamide hydrochloride, dihydrocodeine phosphate, chlophedianol hydrochloride, picoperidamine hydrochloride, cloperastine, isoproterenol hydrochloride, protokylol hydrochloride, salbutamol sulfate, terbutaline sulfate, and the like.

The antidepressants include, for example, phenelzine sulfate, clomipramine, noxiptilin, imipramine, and the like.

The antiepileptics include, for example, ethosuximide, acetazolamide sodium, chlordiazepoxide hydrochloride, and the like.

The muscle relaxants include, for example, pridinol methanesulfonate, pancuronium bromide, tubocurarine chloride, and the like.

The antiulcer agents include, for example, histidine hydrochloride, metoclopramide, and the like.

The antiallergic agents include, for example, ketotifen fumarate, diphenhydramine hydrochloride, chlorpheniramine maleate, methdilazine hydrochloride, tripelennamine hydrochloride, clemizole hydrochloride, diphenylpyraline hydrochloride, methoxyphenamine hydrochloride, and the like.

The hypotensive, diuretic agents include, for example, clonidine hydrochloride, captopril, bunitrolol hydrochloride, hexamethonium bromide, pentolinium, ecarazine hydrochloride, mecamylamine hydrochloride, and the like.

The antidiabetics include, for example, glipizide, glymidine sodium, phenformin hydrochloride, methformin, buformin hydrochloride, and the like.

The cardiotonics include, for example, etilefrine hydrochloride, aminophylline, trans-p-oxocamphor, theophyllol, and the like.

The vasodilating agents include, for example, oxyfedrine hydrochloride, tolazoline hydrochloride, diltiazem hydrochloride, bamethan sulfate, hexobendine, and the like.

The antiarrhythmic agents include, for example, propranolol hydrochloride, oxyprenolol hydrochloride, bufetolol hydrochloride, alprenolol hydrochloride, and the like.

The anticoagulating agents include, for example, heparin sodium, sodium citrate, and the like.

The hemostatic agents include, for example, acetomenaphthone, thrombin, thromboplastin, menadione sodium bisulfate, tranexamic acid, ε-aminocapronic acid, adrenochrome monoaminoguanidine methansulfonate, carbazochrome sodium sulfate, and the like.

The narcotic antagonists include, for example, levallorphan tartrate, naloxone hydrochloride, nalorphine hydrochloride, and the like.

The antitubercular agents include, for example, isoniazid, ethambutol, sodium para-aminosalicylate, and the like.

The hormones include, for example, dexamethasone sodium sulfate, prednisolone sodium phosphate, prednisolone sodium phosphate, prednisolone sodium hemisuccinate, methimazole, betamethasone sodium phosphate, hexestrol phosphate, hexestrol acetate, and the like.

The preparations of the present invention may contain a polylactic acid homopolymer or copolymer matrix and the above-mentioned physiologically active substances in admixture with other pharmaceutically acceptable substances usually used for preparing pharmaceutical preparations such as a solid diluent, a carrier, a binder, an adjuvant and an excipient. Suitable examples of such pharmaceutically acceptable substances are tragacanth, gum arabic, corn starch, gelatin, alginic acid, magnesium stearate, albumin, aluminum monostearate, yellow beeswax, sucrose, lactose, methylparaben, propylparaben, mannitol, propylene glycol, microcrystalline cellulose, calcium silicate, silica, polyvinylpyrrolidone, cacao butter, polyoxyethylene sorbitan monolaurate, ethyl lactate, sorbitan trioleate, ethyl laurate, calcium stearate, talc, oleic acid, linoleic acid, and the like.

The above physiologically active substance may be contained in the pharmaceutical preparations of the present invention in an amount ranging from about 0.01 to about 60% (W/W, hereinafter the same), more preferably from about 0.1 to about 50%, based on an amount of the polylactic acid high molecular weight compound although it may vary depending on the kinds of the employed drug, the desired pharmacological effects, sustained releasing time, and the like.

A size of the microsphere of the present invention is preferably in a range of from several nanometers to several hundred nanometers and can be controlled in accordance with objects, such as easiness for intravenous injection, directing to lymphocyte, easiness for intramuscular injection, or accumulation in a tissue of reticuloendothelial system (RES) such as liver, lung or pancreas. A distribution of the size is preferably as narrow as possible, but an appropriate distribution may be done by sieving.

The polylactic acid of the present invention includes poly-L-lactic acid, poly-D-lactic acid, a copolymer of lactic acid—glycolic acid and the like, and the most suitable polylactic acid can be selected in accordance with a hydrolysis rate, a compatibility with the drug used, or the like, suitable for the objects. The polylactic acid of the present invention may preferably have a weight average molecular weight ranging from 3,000 to 500,000, more preferably from 3,000 to 20,000 (in a range of an oligomer molecule), though the present invention is not limited thereto. Alternatively, in place of the polylactic acid, another polymer which is degradable and absorbable in vivo may also be used, which includes poly-$\beta$-hydroxybutyrate, a copolymer of 3-hydroxybutyrate and 4-hydroxybutyrate, a polydepsipeptide, polydioxanone, a copolymer of lactic acid and a lactone, a copolymer of lactic acid and polyethylene glycol, and the like.

The hydrophilic organic solvent used in the present invention is preferably an organic solvent which is well miscible with water at any ratio but immiscible with a poor solvent of the polylactic acid, including acetonitrile, dioxane, acetone, ethyl alcohol, methyl alcohol, tetrahydrofuran, dimethylformamide, dimethylacetamide, phenol, dimethyl sulfoxide, propyl alcohol, glycerol, ethylene glycol, and the like. Among these, acetonitrile and dioxane are particularly preferable.

The organic acid for dissolving the polylactic acid is preferably acetic acid, formic acid, glycolic acid or lactic acid, most preferably acetic acid. A derivative of acetic acid may also be used, which includes methyl acetate, ethyl acetate, trichloroacetic acid, trifluoroacetic acid, or an acetic acid salt such as sodium acetate, calcium acetate or potassium acetate. When acetic acid is used as the organic acid, it is preferred to use glacial acetic acid. However, in case of a drug hardly soluble in glacial acetic acid such as a protein having a high molecular weight, 80 to 90% acetic acid is preferably employed. On the other hand, when acetonitrile or dioxane is employed as the organic solvent, a mixture of the organic solvent and water is preferably employed in a ratio of 70:30 to 99.9:0.1 (by weight, hereinafter the same), more preferably in a ratio of 80:20 to 95:5 since 100% acetonitrile or dioxane poorly dissolves the polypeptide type active substance.

The poor solvent of the present invention is preferably a solvent which is substantially noncompatible with the solvent for dissolving the physiologically active substance and the polylactic acid and can be readily removed from the preparations after formulating, and includes silicone oil, liquid paraffin, vegetable oils such as cotton oil, sesame oil, castor oil and cone oil, or animal oils such as whale oil, and organic solvents such as toluene, xylene and hexane.

The polylactic acid type microsphere containing the water soluble physiologically active substance according to the present invention can be prepared by the solvent evaporation drying method, that is, by drying in an O/O type emulsion (i.e. oil in oil emulsion) in the case that the mixture of organic solvent/water is used as the solvent, or by drying in a W/O type emulsion (i.e. water in oil emulsion) in the case that acetic acid is used as the solvent. For facilitating the formulation, an emulsifying agent is preferably employed. The emulsifying agent includes any conventional emulsifying agents insofar as they can form a stable O/O or W/O type emulsion and are preferably nonionic surfactants such as those having a HLB of 3 to 6.5, for example, sorbitan monostearate, sorbitan distearate, sorbitan monooleate, sorbitan sesquioleate, sorbitan trioleate, lecithin, and the like. These hydrophobic emulsifying agents are usually added in an amount ranging from 0.1 to 5 parts by weight (hereinafter the same), preferably from 1 to 3 parts, based on 100 parts of the hydrophobic medium. Emulsification can be carried out by any known dispersion procedures, such as a propeller stirring method, a colloid mill method, a homogenizer method, an ultrasonic radiation method or a microfluidizer method. The ultrasonic radiation method is preferably employed in order to obtaine microspheres having a size of several microns. On the other hand, the microfluidizer method is preferably employed in order to obtain microspheres having a size of several tens of nanometer to several hundreds of nanometer.

From the O/O type or W/O type emulsion thus prepared by emulsification procedure such as the ultrasonic radiation method, the solvent for dissolving both polymer and physiologically active substance is distilled off to produce the polylactic acid type microsphere containing the physiologically active substance. The thus obtained microspheres are separated from the poor solvent by means of filtration or centrifugation, washed with an organic solvent such as acetone or hexane to remove the poor solvent remained on the surface of the microspheres, and then dried.

The polylactic acid type microspheres containing a water soluble physiologically active substance according to the present invention can be used in the form of injections, preparations for oral administration, preparations for percutaneous administration, suppositories, preparations for pernasal administration, preparations for administration in the oral cavity, intraocular preparations, and the like.

The polylactic acid type microspheres containing a water soluble physiologically active substance of the present invention is advantageous in that the water soluble physiologically active substance can be uniformly incorporated into the polylactic acid type high molecular weight compound without loss of the activity, whereby occurance of undesirable burst is inhibited and the active substance is gradually released for a long time of period of more than one week and the incorporation rate of the active substance into the microsphere is increased to more than 90%.

The present invention is more specifically illustrated by the following Examples and Comparative Examples but should not be construed to be limited thereto.

EXAMPLE 1

A solution of poly-L-lactic acid having a weight average molecular weight of about 3,600 (1 g) dissolved in acetonitrile (9 ml) was mixed with a solution of adriamycin powder (50 mg) dissolved in distilled water (1 ml) and the mixture was stirred with magnetic stirrer. The obtained solution was added dropwise to cotton oil (100 ml) containing Span 80 (2 wt %) as surfactant while stirring with a propeller type stirrer. After the mixture was heated at 40° to 60° C. to distil off the mixed solvent of acetonitrile and water, the obtained residue was centrifuged and washed with n-hexane to prepare polylactic acid type microspheres containing adriamycin having a mean particle size of 20 to 30 μm. Table 1 shows results of in vitro elution experiment wherein a fixed amount of the microspheres in phosphate buffer (pH 7.4) was placed in an incubator with shaker at 37° C. and the concentration of the active substance was measured by a fluorescent method.

COMPARATIVE EXAMPLE 1

To a solution of poly-L-lactic acid having a weight average molecular weight of about 3,600 (1 g) dissolved in methylene chloride (10 ml) was added adriamycin powder (50 mg) and the mixture was stirred with magnetic stirrer. Thereafter, the procedure of Example 1 was repeated to prepare polylactic acid type microspheres containing adriamycin. Table 1 shows results of the in vitro elution experiment.

EXAMPLE 2

The procedure of Example 1 was repeated except that poly-L-lactic acid having a weight average molecular weight of about 7,500 to prepare poly-L-lactic acid type microspheres containing adriamycin. Table 1 shows results of the in vitro elution experiment.

EXAMPLE 3

The procedure of Example 1 was repeated except that L-lactic acid-glycolic acid copolymer (copolymerization ratio 7:3) having a weight average molecular weight of about 7,000 to prepare poly-L-lactic acid type microspheres containing adriamycin. Table 1 shows results of the in vitro elution experiment.

EXAMPLE 4

A solution of poly-L-lactic acid having a weight average molecular weight of about 3,600 (1 g) dissolved in acetonitrile (9 ml) was mixed with a solution of tobramycin powder (200 mg) dissolved in distilled water (1 ml) and the mixture was stirred with magnetic stirrer. Thereafter the procedure of Example 1 was repeated to prepare polylactic acid type microspheres containing tobramycin. Table 2 shows results of the in vitro elution experiment, which was carried out in the same manner as in Example 1 except that the concentration of the active substance was measured by bioassay procedure using *Bacillus subtilus*.

COMPARATIVE EXAMPLE 2

To a solution of poly-L-lactic acid having a weight average molecular weight of about 3,600 (1 g) dissolved in methylene chloride (10 ml) was added tobramycin powder (200 mg) and the mixture was stirred with magnetic stirrer. Thereafter, the procedure of Example 1 was repeated to prepare polylactic acid type microspheres containing tobramycin. Table 2 shows results of the in vitro elution experiment.

EXAMPLE 5

A solution of poly-L-lactic acid having a weight average molecular weight of about 3,600 (1 g) dissolved in acetonitrile (8 ml) was mixed with a solution of cisplatin (2 mg) dissolved in distilled water (2 ml) and the mixture was stirred with magnetic stirrer. Thereafter, the procedure of Example 1 was repeated to prepare polylactic acid type microspheres containing cisplatin. The incorporation rate of the active substance into microspheres was almost 100%. The in vitro elution experiment was carried out in the same manner as in Example 1 except that the measurement of the elution amount was carried out by atomic absorption spectrometry.

COMPARATIVE EXAMPLE 3

A solution of cisplatin (2 mg) dissolved in 20% aqueous solution of gelatin (2 mg) was added to 20% solution (10 ml) of poly-L-lactic acid having a weight average molecular weight of about 3,600 in methylene chloride and the mixture was emulsified with ultrasonic to prepare a W/O type emulsion, which was cooled quickly to gelate the gelatin layer. The resultant was poured into 1% aqueous solution of polyvinyl alcohol (100 mg) which has previously been ice-cooled, and the mixture was dispersed with a homogenizer to prepare a W/O/W type emulsion. Then, methylene chloride was evaporated and the residue was dried to prepare polylactic acid type microcapsules of gelatin containing cisplatin. The incorporation rate of cisplatin into the microcapsules was only about 29%. Table 2 shows results of the in vitro elution experiment.

EXAMPLE 6

A solution of L-lactic acid-glycolic acid copolymer (copolymerization ratio; 80:20) having a weight average molecular weight of 12,000 (2 g) dissolved in glacial acetic acid (20 ml) and a solution of luteinizing hormone releasing hormone (LHRH; N-Ac[D-P-Cl-Phe[1,2], D-Trp[3], D-Arg[6], D-Ala[10]]LH-RH) (200 mg) dissolved in distilled water (2 ml) were mixed with each other while stirring with magnetic stirrer. The mixture did not become cloudy and remained still clear, showing a complete dissolution of both the polymer and the active substance. This solution was added dropwise to sesame oil (200 ml) containing 1 wt % of lecithin as a surfactant while stirring with a propeller type stirrer and further emulsified with a ultrasonic homogenizer. After acetic acid and water were evaporated with heating at 40° to 60° C., the residue was centrifuged, washed with n-hexane and dried to prepare polylactic acid type microspheres containing LHRH with an average particle size of from 0.5 to 5 μm.

The obtained microspheres were dispersed in refined sesame oil and subcutaneously injected into female rats weighing about 350 g in an amount of 12 mg/kg of LHRH. The effect of LHRH on living body, i.e. atrophy of genital system organ due to desensitization of hypophysis-gonad system, was observed for a long period of time. As a result, the effect continued for about 60 days.

EXAMPLE 7

A solution of poly-L-lactic acid having a weight average molecular weight of 16,000 (2 g) dissolved in glacial acetic acid (20 mg) and a solution of pig insulin (powder manufactured by Sigma, 100 mg) dissolved in 0.1N HCl (2 ml) were mixed with each other while stirring with magnetic stirrer. The mixture did not become cloudy and remained clear. Thereafter, the procedure of Example 6 was repeated to prepare polylactic acid type microspheres containing insulin. Table 3 shows results of the in vitro elution experiment wherein the insulin concentration was measured by glucose oxidase method (enzyme method).

COMPARATIVE EXAMPLE 4

To a solution of polyl-D,L-lactic acid having a weight average molecular weight of 16,000 (2 g) dissolved in chloroform (20 ml) was added insulin powder (100 mg) and the mixture was stirred with magnetic stirrer. Thereafter, the procedure of Example 7 was repeated to prepare a polylactic acid type microspheres containing insulin. Table 3 shows results of the in vitro elution experiment.

EXAMPLE 8

A lactic acid-glycolic acid copolymer (copolymerization ratio; 80:20) having a weight average molecular weight of 7,600 (2 g) and calcitonin (10,000 U) were dissolved in 98% acetic acid (20 ml) while stirring with magnetic stirrer. Thereafter, the procedure of Example 6 was repeated to prepare polylactic acid type microspheres containing calcitonin. Measurement of serum calcium lowering activity proved no decrease of the calcitonin activity. The incorporation rate of calcitonin into polylactic acid type microspheres was about 95%. Table 3 shows results of the in vitro elution experiment wherein the measurement of the elution amount was carried out by HPLC as in Example 1.

COMPARATIVE EXAMPLE 5

The procedure of Comparative Example 3 was repeated except that calcitonin (10,000 U) was used to prepare a W/O/W emulsion and further to prepare a polylactic acid type microcapsules of gelatin containing calcitonin. The incorporation rate of calcitonin into the polylactic acid type microcapsules was about 53%. Table 3 shows results of the in vitro elution experiment.

EXAMPLE 9

A solution of lactic acid-glycolic acid copolymer (copolymerization ratio; 75:25) having a weight average molecular weight of about 5,300 (1 g) and each $1 \times 10^8$ U of mouse interferon α and interferon γ dissolved in 92% acetic acid (10 ml) was added dropwise to sesame oil (100 ml) containing 1 wt % lecithin as surfactant. The mixture was emulsified with microfluidizer (M-110H, manufactured by Microfluidics Corporation) and subjected to drying-in-liquid method to prepare polylactic acid type microspheres containing interferon with an average particle size of from 100 to 500 nm. The incorporation rate of interferon into microspheres was about 98%.

EXAMPLE 10

Meth-A fibrosarcoma cells derived from BALB/C mice were intraperitoneally implanted into BALB/C in an amount of $2 \times 10^6$ cells per animal. Three days after implantation, the polylactic acid type microspheres containing mouse interferon α prepared in Example 9 was intraperitoneally administered into the animal on every third day. Ten days after implantation, the number of Meth-A cells in the abdomen and life-prolonging effect of the mouse were evaluated. The obtained results are shown in Table 4.

COMPARATIVE EXAMPLE 6

The procedure of Comparative Example 3 was repeated except that mouse interferon α ($1 \times 10^8$ U) was used to prepare a W/O/W emulsion and further to prepare a polylactic acid type microcapsules of gelatin containing interferon α. The incorporation rate of interferon into the microcapsule was about 47%. The in vivo experiment was carried out as in Example 10. The results are shown in Table 4.

EXAMPLE 11

The procedure of Example 9 was repeated except that a solution of poly-L-lactic acid having a weight average molecular weight of about 3,600 (500 mg) and human tumor necrosis factor (TNF) ($7.8 \times 10^5$ U) dissolved in 88% acetic acid (10 ml) were used to prepare polylactic acid type microspheres containing TNF. The in vitro elution experiment of Example 1 was repeated where the measurement of elution amount was carried out by enzyme immunoassay. As a result, the activity continued for 30 days.

EXAMPLE 12

The procedure of Example 9 was repeated except that a solution of poly-L-lactic acid having a weight average molecular weight of about 3,600 (500 mg) and human interleukin II ($1 \times 10^6$ U) dissolved in 88% acetic acid (10 ml) were used to prepare polylactic acid type microspheres containing interleukin II.

The obtained microspheres were injected into mouse blood and the blood level of IL-II was measured by using IL-II dependent cell line, CTLL-2. The result showed a high concentration of IL-II of not less than $1 \times 10^3$ U/ml for 96 hours.

EXAMPLE 13

The procedure of Example 6 was repeated except that a solution of poly-L-lactic acid having a weight average molecular weight of about 3,600 (500 mg) and rat epidermal growth factor (EGF) (0.5 mg) dissolved in 90% acetic acid (20 ml) were used to prepare polylactic acid type microspheres containing EGF.

The obtained microspheres were subcutaneously administered to carotide-intubated rat and the serum level of EGF was measured by radioimmunoassay. The result showed an increase of the serum level of EGF which was found on the second day and continued for about 30 days.

EXAMPLE 14

The procedure of Example 6 was repeated except that a solution of poly-L-lactic acid having a weight average molecular weight of about 3,600 (500 mg) and urokinase ($6 \times 10^5$ U) dissolved in glacial acetic acid were used to prepare polylactic acid type microspheres containing urokinase. The in vitro elution experiment was carried out and the enzyme activity was measured by fibrin plate method. The result showed urokinase of not less than 1,000 U for about 4 weeks.

EXAMPLE 15

The procedure of Example 6 was repeated except that a solution of poly-L-lactic acid having a weight average molecular weight of about 3,600 (500 mg) and prolactin (100 mg) dissolved in glacial acetic acid were used to prepare polylactic acid type microspheres containing prolactin. The obtained microspheres were subcutaneously administered to rat and the serum level of prolactin was measured by radioimmunoassay. The result showed a high concentration of prolactin for about 60 days.

EXAMPLE 16

The procedure of Example 1 was repeated except that a solution of poly-L-lactic acid having a weight average molecular weight of about 4,700 (1 g) and panimycin (dibekacin sulfate) (100 mg) dissolved in a mixture of acetonitrile and water (9:1) (20 ml) were used to prepare polylactic acid type microspheres containing panimycin. The obtained microspheres were subjected to the in vitro elution experiment wherein the duration of the antimicrobial activity was measured by bioassay using *Bacillus subtilis*. The result proved that a high concentration of not less than 10 μg/ml of panimycin was continued for about 30 days.

TABLE 1

| Elution | Cumulative elution of adriamycin (%) | | | |
|---|---|---|---|---|
| (day) | Ex. 1 | Ex. 2 | Ex. 3 | Comp. Ex. 1 |
| 1 | 24.5 | 9.3 | 12.2 | 33.6 |
| 3 | 28.1 | 11.7 | 24.3 | 91.3 |
| 4 | 37.3 | 20.2 | 31.6 | 100.0 |
| 14 | 56.6 | 29.3 | 42.6 | — |
| 21 | 78.2 | 41.5 | 55.1 | — |
| 28 | 89.4 | 53.8 | 67.3 | — |
| 42 | 100.0 | 69.1 | 81.7 | — |
| 56 | — | 84.6 | 100.0 | — |
| 68 | — | 100.0 | — | — |

TABLE 2

| Elution | Cumulative elution of tobramycin (%) | | Cumulative elution of cisplatin (%) | |
|---|---|---|---|---|
| (day) | Ex. 4 | Comp. Ex. 2 | Ex. 5 | Comp. Ex. 3 |
| 1 | 29.5 | 93.5 | 21.7 | 35.4 |
| 3 | 42.1 | 100.0 | 35.4 | 86.5 |
| 7 | 65.7 | — | 53.2 | 100.0 |
| 14 | 83.5 | — | 71.7 | — |
| 28 | 91.4 | — | 95.3 | — |
| 42 | 100.0 | — | 100.0 | — |

TABLE 3

| Elution | Cumulative elution of insulin (%) | | Cumulative elution of calcitonin (%) | |
|---|---|---|---|---|
| (day) | Ex. 7 | Comp. Ex. 4 | Ex. 8 | Comp. Ex. 5 |
| 1 | 21.2 | 71.3 | 13.6 | 51.3 |
| 4 | 48.3 | 100.0 | 23.5 | 92.4 |
| 8 | 63.5 | — | 49.7 | 100.0 |
| 12 | 74.7 | — | 66.9 | — |
| 16 | 87.9 | — | 91.2 | — |
| 20 | 96.3 | — | 98.5 | — |

TABLE 4

| | Meth-A cell No. ($\times 10^5$) | Survival date (day) |
|---|---|---|
| Ex. 10 | 405 ± 263 | 60 |
| Ex. 6 | 952 ± 287 | 14 |

What is claimed is:

1. A process for preparing microspheres comprising a polylactic acid and a water soluble physiologically active substance, which comprises:
    preparing a solution of the water soluble physiologically active substance and the polylactic acid uniformly dissolved in (i) a mixed solvent comprising acetonitrile and water or (ii) an aqueous solution of acetic acid; mixing the solution with a poor solvent which is immiscible with said mixed solvent or said aqueous solution of acetic acid to give an O/O type or W/O type emulsion; and subjecting said resultant emulsion to solvent evaporation drying to produce said microspheres.

2. The process of claim 1 wherein said polylactic acid is a member selected from the group consisting of a L-lactic acid polymer, a D,L-lactic acid polymer, a copolymer of L-lactic acid and glycolic acid and a copolymer of D,L-lactic acid and glycolic acid.

3. The process of claim 1, wherein said poor solvent which is immiscible with said mixed solvent or said aqueous solution of acetic acid is a member selected from the group consisting of silicone oil, liquid paraffin, cotton oil, sesame oil, castor oil, cone oil, whale oil, toluene, xylene and hexane.

4. The process according to claim 1 wherein said produced microspheres have a mean particle size of from about 0.01 μm to 300 μm.

5. Microspheres produced according to the process of claim 1.

6. A process for preparing microspheres comprising a polylactic acid matrix and a water soluble physiologically active substance, which comprises:
    preparing a solution of the water soluble physiologically active substance and a polylactic acid uniformly dissolved in a mixed solvent comprising acetonitrile and water or dissolved in an aqueous solution of acetic acid;
    mixing said solution with a poor solvent which is immiscible with said mixed solvent or said aqueous solution of acetic acid to give an O/O type or W/O type emulsion; and
    subjecting said resultant emulsion to solvent evaporation drying to produce said microspheres which comprise said polylactic acid matrix with said water soluble physiologically active substance uniformly distributed therein whereby occurrence of undesirable burst is inhibited and the active substance is gradually released from more than one week.

* * * * *